United States Patent
Agnihotri et al.

(10) Patent No.: US 7,804,934 B2
(45) Date of Patent: Sep. 28, 2010

(54) ACCURATE MEASUREMENT OF LAYER DIMENSIONS USING XRF

(75) Inventors: Dileep Agnihotri, Round Rock, TX (US); Jeremy O'Dell, Manor, TX (US); Isaac Mazor, Haifa (IL); Boris Yokhin, Nazareth Illit (IL)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 66 days.

(21) Appl. No.: 12/272,050

(22) Filed: Nov. 17, 2008

(65) Prior Publication Data

US 2009/0074137 A1    Mar. 19, 2009

Related U.S. Application Data

(63) Continuation-in-part of application No. 11/889,337, filed on Aug. 10, 2007, now abandoned, which is a continuation of application No. 11/610,174, filed on Dec. 13, 2006, now abandoned, application No. 12/272,050, filed on Nov. 17, 2008, and a continuation-in-part of application No. 11/487,433, filed on Jul. 17, 2006, now Pat. No. 7,483,513, which is a continuation of application No. 11/018,352, filed on Dec. 22, 2004, now Pat. No. 7,110,491.

(60) Provisional application No. 60/753,895, filed on Dec. 23, 2005.

(51) Int. Cl.
*G01N 23/223* (2006.01)
*G01T 1/36* (2006.01)

(52) U.S. Cl. .......................... 378/50; 378/44

(58) Field of Classification Search ................ 378/43, 378/44, 50, 51, 54, 70, 86, 87, 89, 90; 438/14, 438/16, 959; 257/797; 382/145, 147, 149, 382/152; 430/290, 311–331, 395
See application file for complete search history.

(56) References Cited

U.S. PATENT DOCUMENTS 3,256,431 A    6/1966    Fraser (Continued)

FOREIGN PATENT DOCUMENTS

JP    10048398 A    2/1998

(Continued)

OTHER PUBLICATIONS

Dane et al., "Application of Genetic Algorithms for Characterization of Thin Layered Materials by Glancing Incidence X-Ray Reflectometry", Physica B 253, pp. 254-268, 1998 Elsevier Science B.V.

Huang et al., "Characterization of Single- and Multiple-Layer Films by X-Ray Reflectometry", Advances in X-Ray Analysis, vol. 35, pp. 137-142, Plenum Press, New York, USA, 1992.

Kozaczek et al., "X-Ray Diffraction Metrology for 200 MM Process Qualification and Stability Assessment", Advanced Metallization Conference, Montreal, Canada, Oct. 8-11, 2001.

(Continued)

*Primary Examiner*—Edward J Glick
*Assistant Examiner*—Anastasia Midkiff
(74) *Attorney, Agent, or Firm*—D. Kligler IP Services Ltd.; Daniel Kligler (57) ABSTRACT

A method for inspection of a sample includes directing an excitation beam to impinge on an area of a planar sample that includes a feature having sidewalls perpendicular to a plane of the sample, the sidewalls having a thin film thereon. An intensity of X-ray fluorescence (XRF) emitted from the sample responsively to the excitation beam is measured, and a thickness of the thin film on the sidewalls is assessed based on the intensity. In another method, the width of recesses in a surface layer of a sample and the thickness of a material deposited in the recesses after polishing are assessed using XRF.

18 Claims, 4 Drawing Sheets

U.S. PATENT DOCUMENTS

| | | |
|---|---|---|
| 3,581,087 A | 5/1971 | Brinkerhoff et al. |
| 3,919,548 A | 11/1975 | Porter |
| 3,980,568 A | 9/1976 | Pitchford et al. |
| 4,048,496 A | 9/1977 | Albert |
| 4,085,329 A | 4/1978 | McCoy et al. |
| 4,446,568 A | 5/1984 | Williams et al. |
| 4,590,603 A | 5/1986 | Relihan et al. |
| 4,710,259 A | 12/1987 | Howe et al. |
| 4,718,075 A | 1/1988 | Horn |
| 4,725,963 A | 2/1988 | Taylor et al. |
| 4,847,882 A | 7/1989 | Knoth et al. |
| 4,852,135 A | 7/1989 | Anisovitch et al. |
| 4,916,720 A | 4/1990 | Yamamoto et al. |
| 4,989,226 A | 1/1991 | Woodbury et al. |
| 5,151,588 A | 9/1992 | Firi et al. |
| 5,425,066 A | 6/1995 | Takahashi et al. |
| 5,481,109 A | 1/1996 | Ninomiya et al. |
| 5,497,008 A | 3/1996 | Kumakhov |
| 5,574,284 A | 11/1996 | Farr |
| 5,619,548 A | 4/1997 | Koppel |
| 5,740,226 A | 4/1998 | Komiya et al. |
| 5,742,658 A | 4/1998 | Tiffin et al. |
| 5,778,039 A | 7/1998 | Hossain et al. |
| 5,900,645 A | 5/1999 | Yamada |
| 5,909,276 A | 6/1999 | Kinney et al. |
| 5,923,720 A | 7/1999 | Barton et al. |
| 5,937,026 A | 8/1999 | Satoh |
| 5,949,847 A | 9/1999 | Terada et al. |
| 5,963,329 A | 10/1999 | Conrad et al. |
| 6,040,095 A | 3/2000 | Enichen et al. |
| 6,041,098 A | 3/2000 | Touryanski et al. |
| 6,108,398 A | 8/2000 | Mazor et al. |
| 6,173,036 B1 | 1/2001 | Hossain et al. |
| 6,192,103 B1 | 2/2001 | Wormington et al. |
| 6,226,347 B1 | 5/2001 | Golenhofen |
| 6,226,349 B1 | 5/2001 | Shushter et al. |
| 6,266,389 B1 | 7/2001 | Murayama et al. |
| 6,345,086 B1 | 2/2002 | Ferranolino et al. |
| 6,351,516 B1 | 2/2002 | Mazor et al. |
| 6,381,303 B1 | 4/2002 | Vu et al. |
| 6,389,102 B2 | 5/2002 | Francke et al. |
| 6,453,002 B1 | 9/2002 | Mazor et al. |
| 6,453,006 B1 | 9/2002 | Koppel et al. |
| 6,507,634 B1 | 1/2003 | Koppel et al. |
| 6,512,814 B2 | 1/2003 | Yokhin et al. |
| 6,556,652 B1 | 4/2003 | Mazor et al. |
| 6,639,968 B2 | 10/2003 | Yokhin et al. |
| 6,643,354 B2 | 11/2003 | Koppel et al. |
| 6,680,996 B2 | 1/2004 | Yokhin et al. |
| 6,704,661 B1 | 3/2004 | Opsal et al. |
| 6,711,232 B1 | 3/2004 | Janik |
| 6,744,850 B2 | 6/2004 | Fanton et al. |
| 6,750,952 B2 | 6/2004 | Grodnensky et al. |
| 6,754,304 B1 | 6/2004 | Kumakhov |
| 6,754,305 B1 | 6/2004 | Rosencwaig et al. |
| 6,771,735 B2 | 8/2004 | Janik et al. |
| 680,105 A1 | 10/2004 | Nasser-Ghodsi et al. |
| 6,823,043 B2 | 11/2004 | Fewster et al. |
| 6,879,051 B1 | 4/2005 | Singh et al. |
| 6,890,575 B2 | 5/2005 | Beauregard et al. |
| 6,947,520 B2 | 9/2005 | Yokhin |
| 6,977,986 B1 | 12/2005 | Beanland et al. |
| 7,023,954 B2 | 4/2006 | Rafaeli et al. |
| 7,062,013 B2 | 6/2006 | Berman et al. |
| 7,068,753 B2 | 6/2006 | Berman et al. |
| 7,071,007 B2 | 7/2006 | Tseng et al. |
| 7,103,142 B1 | 9/2006 | Agnihotri et al. |
| 7,110,491 B2 | 9/2006 | Mazor et al. |
| 7,120,228 B2 | 10/2006 | Yokhin et al. |
| 7,130,376 B2 | 10/2006 | Berman et al. |
| 7,600,916 B2 * | 10/2009 | Yokhin et al. ............... 378/205 |
| 2001/0028699 A1 | 10/2001 | Iwasaki |
| 2001/0043668 A1 | 11/2001 | Hayashi et al. |
| 2002/0097837 A1 | 7/2002 | Fanton et al. |
| 2002/0110218 A1 | 8/2002 | Koppel et al. |
| 2003/0012337 A1 | 1/2003 | Fewster et al. |
| 2003/0128809 A1 | 7/2003 | Umezawa et al. |
| 2003/0157559 A1 | 8/2003 | Omote et al. |
| 2004/0052330 A1 | 3/2004 | Koppel et al. |
| 2004/0109531 A1 | 6/2004 | Yokhin et al. |
| 2004/0131151 A1 | 7/2004 | Berman et al. |
| 2004/0156474 A1 | 8/2004 | Yokhin et al. |
| 2004/0218717 A1 | 11/2004 | Koppel et al. |
| 2004/0267490 A1 | 12/2004 | Opsal et al. |
| 2006/0062350 A1 | 3/2006 | Yokhin et al. |
| 2006/0062351 A1 | 3/2006 | Yokhin et al. |
| 2006/0227931 A1 | 10/2006 | Mazor et al. |
| 2006/0274886 A1 | 12/2006 | Mazor et al. |
| 2008/0049895 A1 | 2/2008 | Agnihotri et al. |
| 2008/0159475 A1 | 7/2008 | Mazor et al. |

FOREIGN PATENT DOCUMENTS

| | | | |
|---|---|---|---|
| JP | 10318949 A | | 12/1998 |
| JP | 2004151004 A | * | 5/2004 |
| WO | 01/24200 A1 | | 4/2001 |

OTHER PUBLICATIONS

EX-6500 Advanced EDXRF Spectrometer manufactures by Jordan Valley Semiconductors, 2000.

Powell et al., "X-Ray Diffraction and Reflectivity Characterization of SiGe Superlattice Structures", Semiconductor Science and Technology, edition 7, pp. 627-631, IOP Publishing Ltd., UK, 1992.

Lengeler, Bruno, "X-Ray Reflection, a New Tool for Investigating Layered Structures and Interfaces", Advances in X-Ray Analysis, vol. 35, pp. 127-135, Plenum Press, New York, USA, 1992.

Lankosz et al., "Research in Quantitative X-Ray Fluorescence Microanalysis of Patterned Thin Films", Advances in X-Ray Analysis, vol. 43, pp. 497-503, 48th Annual Denver X-Ray Conference, Steamboat Springs, Colorado, USA, Aug. 2-6, 1999.

Levine Parrill et al., "GISAXS—Glancing Incidence Small Angles X-Ray Scattering", Journal de Physique IV, supplement to Journal de Physique I, vol. 3, pp. 411-417, Dec. 1993.

Neissendorfer et al., "The Energy-Dispersive Reflectometer/Diffractometer at BESSY-I", Measurement Science and Technology Journal, edition 10, pp. 354-361, IOP Publishing Ltd., UK, 1999.

Bowen et al., "X-Ray Metrology by Diffraction and Reflectivity", 2000 International Conference on Characterization and Metrology for ULSI Technology, NIST, Gaithersburg, Maryland, USA, Jun. 26-29, 2000.

Ulyanenkov, Alex, "Introduction to High Resolution X-Ray Diffraction", Workshop on X-Ray Characterization of Thin Layers, Uckley, May 21-23, 2003.

Naudon et al., "New Apparatus for Grazing X-Ray Reflectometry in the Angle-Resolved Dispersive Mode", Journal of Applied Crystallography, vol. 22, pp. 460-464, International Union of Crystallography, 1989.

X-Ray Optical Systems, Inc., "Monolithic Polycapillary Lens Information", Albany, USA, Dec. 29, 1998.

U.S. Appl. No. 60/753,895 "Accurate Measurement of Layer Dimensions Using XRF"0 filed on Dec. 22, 2005.

U.S. Appl. No. 60/800,589 "Automated Selection of X-Ray Reflectometry Measurement Locations" filed on May 15, 2006.

U.S. Appl. No. 11/018,352 Official Action dated Feb. 8, 2006.
U.S. Appl. No. 11/889,337 Official Action dated Jul. 24, 2008.
U.S. Appl. No. 11/018,352 Official Action dated Oct. 24, 2005.
U.S. Appl. No. 11/487,433 Official Action dated May 29, 2008.
U.S. Appl. No. 12/003,215 Official Action dated Apr. 1, 2009.
U.S. Appl. No. 11/103,071 Official Action dated Oct. 5, 2006.
U.S. Appl. No. 09/028,588 Official Action dated Jun. 4, 1999.

Agnihotri, D., U.S. Appl. No. 11/610,174 "Accurate Measurement of Layer Dimensions Using XRF", filed on Dec. 13, 2006 (abandoned).

Singer, P., "Copper CMP: Taking Aim at Dishing", Semiconductor International, Oct. 1, 2004 (http://www.semiconductor.net/article/200524-Copper_CMP_Taking_Aim_at_Dishing.php).

Jones et al., "Small Angle X-Ray Scattering for Sub-100 nm Pattern Characterization", Applied Physics Letters, vol. 83, No. 19, pp. 4059-4061, American Institute of Physics, Nov. 10, 2003.

Hu et a., "Small Angle X-Ray Scattering Metrology for Sidewall Angle and Cross Section of Nanometer Scale Line Gratings", Journal of Applied Physics, vol. 96, No. 4, pp. 1983-1987, American Institute of Physics, Aug. 15, 2004.

Wu et al., "Small Angle Neutron Scattering Measurements of Nanoscale Lithographic Features",, Polymer Preprints 42 (1), pp. 265-266, 2001.

Kojima et al., "Structural Characterization of Thin Films by X-Ray Reflectivity", Rigaku Journal, vol. 16, No. 2, pp. 31-41, 1999.

X-Ray Optical Systems, Inc., "Micro X-Ray Fluorescence With Focusing Polycapillary Optics", Application Note 102, USA, 2002 (http://www.xos.com/wp-content/uploads/PCFocusingapp2228.pdf).

Guerault, H., "Specular Reflectivity and Off-Specular Scattering: Tools for roughness investigation",Instituut voor Kern- en Stralingsfysica, Dec. 15, 2000.

Wiener et al., "Characterization of Titanium Nitride Layers by Grazing-Emission X-Ray Fluorescence Spectrometry", Applied Surface Science 125, pp. 129-136, Elsevier Science B.V.1998.

Hayashi et al., "Refracted X-Rays Propagating Near the Surface Under Grazing Incidence Condition", Spectrochimics Acts Part B 54, pp. 227-230, Elsevier Science B.V. 1999.

Di Fonzo et al., "Non-Destructive Determination of Local Strain With 100-Nanometre Spatial Resolution", Nature, vol. 403, February 2000 (www.nature.com).

\* cited by examiner

ACCURATE MEASUREMENT OF LAYER DIMENSIONS USING XRF

CROSS-REFERENCE TO RELATED APPLICATION

This application is a continuation-in-part of U.S. patent application Ser. No. 11/889,337, filed Aug. 10, 2007, which is a continuation of U.S. patent application Ser. No. 11/610,174, filed Dec. 13, 2006 (abandoned), which claims the benefit of U.S. Provisional Patent Application 60/753,895, filed Dec. 22, 2005. This application is also a continuation-in-part of U.S. patent application Ser. No. 11/487,433, filed Jul. 17, 2006, which is a continuation of U.S. patent application Ser. No. 11/018,352, filed Dec. 22, 2004 (now U.S. Pat. No. 7,110,491). The disclosures of all of the aforementioned related applications are incorporated herein by reference.

FIELD OF THE INVENTION

The present invention relates generally to non-destructive testing, and particularly to methods and systems for testing of thin film layers formed in the production of semiconductor devices.

BACKGROUND OF THE INVENTION

X-ray fluorescence (XRF) measurement, and specifically X-ray microfluorescence (i.e., X-ray fluorescence using narrow, focused excitation beams), is gaining increasing attention as a method for testing semiconductor wafers. XRF itself is a well-known technique for determining the elemental composition of a sample. XRF analyzers generally include an X-ray source, which irradiates the sample, and an X-ray detector, for detecting the X-ray fluorescence emitted by the sample in response to the irradiation. Each element in the sample emits X-ray fluorescence in energy bands that are characteristic of the element. The detected X-ray fluorescence is analyzed to find the energies or, equivalently, the wavelengths of the detected photons, and the qualitative and/or quantitative composition of the sample is determined based on this analysis.

U.S. Pat. No. 6,108,398, for example, whose disclosure is incorporated herein by reference, describes an XRF analyzer and a method for analyzing a sample. The analyzer includes an X-ray beam generator, which generates an X-ray beam incident at a spot on the sample and creates a plurality of fluorescent X-ray photons. An array of semiconductor detectors is arranged around the spot so as to capture the fluorescent X-ray photons. The analyzer produces electrical pulses suitable for analysis of the sample.

The use of X-ray microfluorescence for testing semiconductor wafers is described in U.S. Pat. No. 6,351,516, whose disclosure is incorporated herein by reference. This patent describes a non-destructive method for testing the deposition and/or the removal of a material within a recess on the surface of a sample. An excitation beam is directed onto a region of the sample in a vicinity of the recess, and an intensity of X-ray fluorescence emitted from the region is measured. A quantity of the material that is deposited within the recess is determined responsively to the measured intensity.

Another application of X-ray microfluorescence is described by Lankosz et al., in a paper entitled "Research in Quantitative X-ray Fluorescence Microanalysis of Patterned Thin Films," *Advances in X-ray Analysis* 43 (1999), pages 497-503, which is incorporated herein by reference. The authors describe a method for X-ray fluorescence microanalysis using a collimated micro-beam. The method is applied for testing the thickness and uniformity of thin films prepared by ion sputtering techniques.

U.S. Pat. No. 6,556,652, whose disclosure is incorporated herein by reference, describes a method for measurement of critical dimensions by irradiating a surface of a substrate with a beam of X-rays. A pattern of the X-rays scattered from the surface due to features formed on the surface is detected and analyzed to measure a dimension of the features in a direction parallel to the surface. Typically, the substrate comprises a semiconductor wafer, on which a test pattern is formed for the purpose of measuring critical dimensions of functional features of microelectronic devices in fabrication on the wafer. In one embodiment, the test pattern comprises a grating structure, made up of a periodic pattern of ridges, having attributes (such as height, width and spacing) similar to those of the functional features in question.

U.S. Pat. No. 6,879,051, whose disclosure is incorporated herein by reference, describes a method for determining see layer thickness of trench sidewalls. The method involves forming a conformal seed layer over a barrier layer in a trench that is formed in a substrate. A beam of X-rays is directed at the seed layer sidewall portions, and the reflected X-ray signal is measured in order to determine the thickness of the sidewall portions.

SUMMARY OF THE INVENTION

Embodiments of the present invention provide improved methods for measuring dimensions of structures on a substrate using X-ray techniques, and specifically using XRF. In some embodiments, for example, these techniques are used in determining critical dimensions of features that are formed on a semiconductor wafer. Additionally or alternatively, embodiments of the present invention may be applied to determine the thickness of thin-film layers deposited on a substrate, and particularly of layers deposited on the sidewalls of structures formed on the substrate. ("Sidewalls" in this context refers to the parts of the structure that are perpendicular, or at least not parallel, to the plane of the surface of the substrate.)

Further aspects of sidewall measurement using X-ray scattering are described in U.S. Pat. No. 7,110,491. The use of XRF in evaluating deposition and processing of layers on semiconductor wafers is also described in U.S. Patent Application Publication 2006/0227931. The disclosures of both of these references, which are assigned to the assignee of the present patent application, are incorporated herein by reference. The techniques described in these two references, as well as in the publications cited in the Background of the Invention, may be advantageously applied in conjunction with the methods and systems that are described hereinbelow.

There is therefore provided, in accordance with an embodiment of the present invention, a method for inspection of a sample including:

directing an excitation beam to impinge on an area of a planar sample that includes a feature having sidewalls perpendicular to a plane of the sample, the sidewalls having a thin film thereon;

measuring an intensity of X-ray fluorescence (XRF) emitted from the sample responsively to the excitation beam; and assessing a thickness of the thin film on the sidewalls based on the intensity.

In disclosed embodiments, the thin film is applied to at least one horizontal surface of the sample, in addition to the sidewalls, and assessing the thickness includes determining a depth of the thin film on the at least one horizontal surface, and calculating the thickness of the thin film on the sidewalls based on both the depth and the intensity. Determining the depth may include measuring X-ray reflectance from the at least one horizontal surface. Alternatively or additionally, determining the depth includes depositing the thin film on a reference area of the planar sample that does not contain the sidewalls, and measuring the depth of the thin film on the reference area.

In some embodiments, the area of the planar sample includes a first region having one or more recesses formed in a first pattern in a surface layer thereof, and the method includes directing the excitation beam to impinge on a second region of the planar sample having a second pattern of recesses, which is different from the first pattern, and assessing the thickness includes comparing first and second intensities of the XRF emitted from the first and second regions, respectively.

In other embodiments, the sidewalls include a first element, which emits the XRF in a first XRF spectral line, and a second element is also deposited on the area of the planar sample, the second element having second and third XRF spectral lines, wherein the third XRF spectral line overlaps the first XRF spectral line, and assessing the thickness includes measuring a ratio of a first intensity of the XRF measured in a first spectral region including the first and third XRF spectral lines to a second intensity of the XRF measured in a second region including the second XRF spectral line, and calculating the thickness based on the measured ratio. I one embodiment, calculating the thickness includes comparing the measured ratio to a reference ratio determined for the second element in absence of the first element, wherein the first element is tantalum, and the second element is copper.

There is also provided, in accordance with an embodiment of the present invention, a method for processing a sample, including:

depositing a material over first and second regions of the sample, the first region having one or more recesses formed in a first pattern in a surface layer thereof, while the second region is characterized by a second pattern of recesses, which is different from the first pattern;

polishing the sample after depositing the material so as to remove a portion of the material from the sample;

after polishing the sample, directing an excitation beam onto the first and second regions;

measuring first and second intensities of X-ray fluorescence emitted responsively to the excitation beam from the first and second regions, respectively, in a spectral range in which the material is known to fluoresce; and assessing both a thickness of the material deposited in the recesses in the first pattern and a width of the recesses in the first pattern based on the first and second intensities.

The method may include, prior to polishing the sample, directing the excitation beam onto at least the second region and measuring a third intensity of the X-ray fluorescence emitted responsively to the excitation beam, and determining a quantity of the material removed by the polishing based on a difference between the second and third intensities.

In a disclosed embodiment, the second pattern is planar and contains none of the recesses. Optionally, the method includes measuring a third intensity of the X-ray fluorescence emitted responsively to the excitation beam from a third region on which the material is not deposited, and assessing both the thickness and the width includes using the measured third intensity as a zero reference in determining the thickness and the width.

Typically, the recesses in the first region are formed so as to define at least one feature selected from a group of features consisting of lines, pads, tiles and through-holes.

There is additionally provided, in accordance with an embodiment of the present invention apparatus for inspection of a sample, including:

an excitation source, which is configured to direct an excitation beam to impinge on an area of a planar sample that includes a feature having sidewalls perpendicular to a plane of the sample, the sidewalls having a thin film thereon;

one or more detectors, which are arranged to measure an intensity of X-ray fluorescence (XRF) emitted from the sample responsively to the excitation beam; and a signal processor, which is operative to assess a thickness of the thin film on the sidewalls based on the intensity.

There is further provided, in accordance with an embodiment of the present invention, apparatus for processing a sample, including:

a deposition station, which is arranged to deposit a material over first and second regions of the sample, the first region having one or more recesses formed in a first pattern in a surface layer thereof, while the second region is characterized by a second pattern of recesses, which is different from the first pattern;

a polishing station, which is arranged to polish the sample after depositing the material so as to remove a portion of the material from the sample; and a test station, which is arranged to direct an excitation beam onto the first and second regions after polishing of the sample, to measure first and second intensities of X-ray fluorescence emitted responsively to the excitation beam from the first and second regions, respectively, in a spectral range in which the material is known to fluoresce, and to assess both a thickness of the material deposited in the recesses in the first pattern and a width of the recesses in the first pattern based on the first and second intensities.

There is moreover provided, in accordance with an embodiment of the present invention, apparatus for inspection of a sample, including:

an excitation source, which is configured to direct an excitation beam onto first and second regions of the sample after deposition of a material over the first and second regions of the sample, the first region having one or more recesses formed in a first pattern in a surface layer thereof, while the second region is characterized by a second pattern of recesses, which is different from the first pattern, and after polishing of the sample so as to remove a portion of the material from the sample following the deposition of the material;

one or more detectors, which are arranged to measure first and second intensities of X-ray fluorescence emitted responsively to the excitation beam from the first and second regions, respectively, in a spectral range in which the material is known to fluoresce; and a signal processor, which is operative to assess both a thickness of the material deposited in the recesses in the first pattern and a width of the recesses in the first pattern based on the first and second intensities.

The present invention will be more fully understood from the following detailed description of the embodiments thereof, taken together with the drawings in which:

DETAILED DESCRIPTION OF EMBODIMENTS

Figure 1:
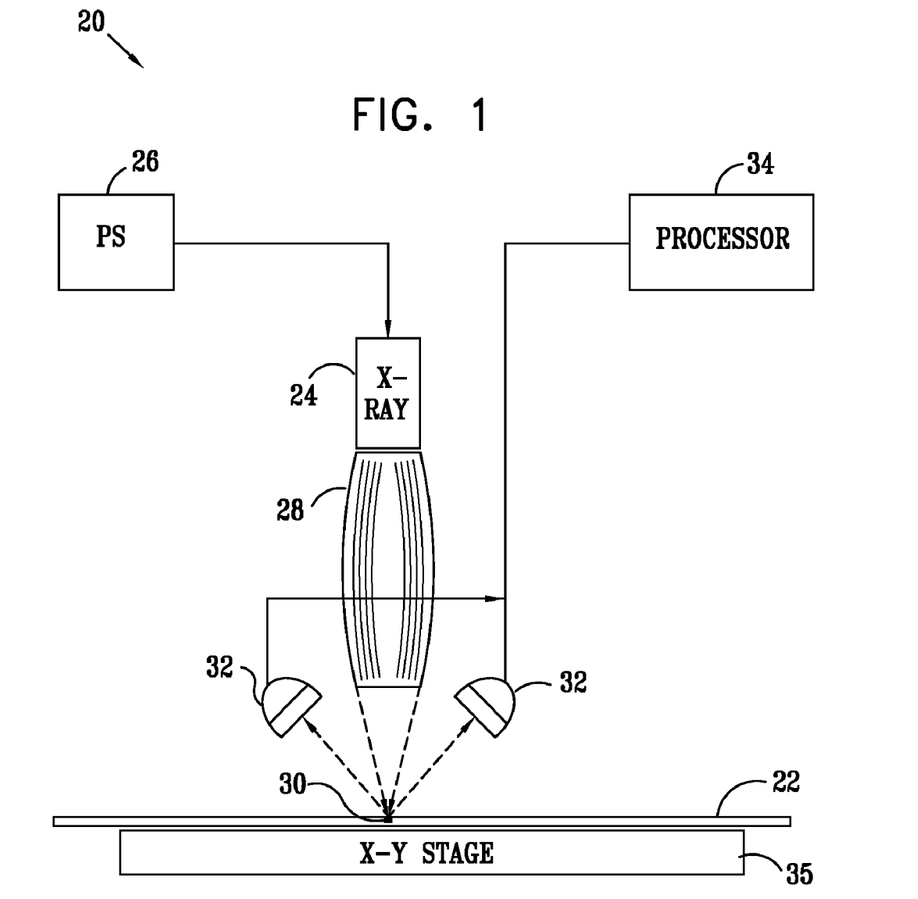
FIG. 1 is a schematic illustration of a system for X-ray microfluorescence measurement, in accordance with an embodiment of the present invention.

FIG. 1 is a schematic illustration of an X-ray microfluorescence analyzer 20, in accordance with an embodiment of the present invention. Aspects of analyzer 20 are described in detail in the above-mentioned U.S. Pat. No. 6,108,398. Analyzer 20 is arranged to examine a semiconductor wafer 22 (or another sample), in order to identify faults in the wafer fabrication process, using methods described hereinbelow.

Analyzer 20 typically comprises an excitation source, such as an X-ray tube 24, driven by a high-voltage power supply 26, as is known in the art. The X-ray tube emits X-rays having a suitable energy range and power flux into X-ray optics 28. The optics may comprise a polycapillary array, for example. Optics 28 focus the X-ray beam onto a small region 30, typically a spot on the order of 20 µm in diameter, on the surface of sample 22. The irradiated region emits fluorescent X-rays, which are captured by an array of detectors 32 arranged around region 30 and angled toward it. Responsively to the captured photons, detectors 32 generate electrical signals, which are conveyed to a signal processor 34.

Alternatively, other types of fluorescence analyzers known in the art, comprising any suitable excitation source, power source, focusing optics and detection system, may be used for implementing the methods described herein.

Processor 34 typically comprises an energy-dispersive pulse processing system, as is known in the art, which determines an intensity spectrum of the X-ray photons captured by the detectors. Alternatively, a wavelength-dispersive detection and processing system may be used. Each chemical element within the irradiated region that is excited by the X-rays from tube 24 emits X-rays in characteristic spectral lines. The intensity of the characteristic spectral lines of a given element is proportional to the mass of that element within region 30. Thus, processor 34 uses the determined intensity spectra to determine how much of a particular material is present within the area of region 30. Processor 34 typically comprises a general-purpose computer, which performs these functions under the control of suitable software. The software may be downloaded to the processor in electronic form, over a network, for example, or it may alternatively be provided on tangible media, such as optical, magnetic or electronic memory media.

As shown in FIG. 1, analyzer 20 is used to examine region 30 on wafer 22. In one embodiment, the sample is mounted on a movable platform, such as an X-Y stage 35, so as to enable the wafer to be moved with respect to the X-ray beam. Alternatively, the wafer is mounted on a suitable stationary fixture while tube 24, optics 28 and detectors 32 are moved, so that the X-ray beam scans the wafer.

Analyzer 20 may be further configured to capture and process X-rays scattered from wafer 22 by other mechanisms, such as reflection, diffraction, and/or small-angle scattering. Multi-function systems of this sort are described, for example, in U.S. Pat. Nos. 6,381,303 and 6,895,075 and in U.S. patent application Ser. No. 11/200,857, filed Aug. 10, 2005, which is assigned to the assignee of the present patent application. The disclosures of these patents and of this patent application are incorporated herein by reference.

Figure 2:
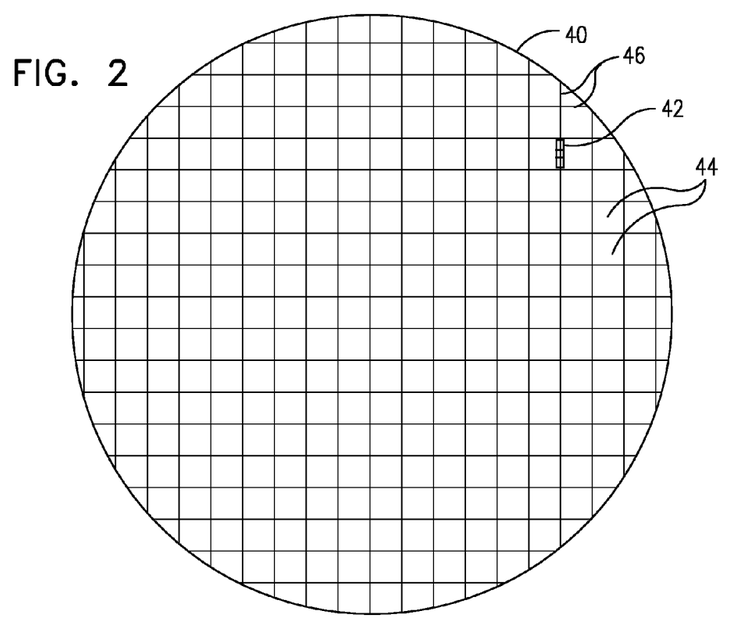
FIG. 2 is a schematic top view of a semiconductor wafer having a test pattern formed thereon, in accordance with an embodiment of the present invention.

Reference is now made to FIG. 2, which is a schematic top view of a semiconductor wafer 40, typically a silicon wafer, on which a test pattern 42 is formed, in accordance with an embodiment of the present invention. The wafer is divided into multiple dies 44, which are separated by scribe lines 46. Pattern 42 is typically positioned on one of the scribe lines, and is narrow enough, typically on the order of 75 µm across, so as not to impinge significantly on the dies to either side of the line. Optionally, multiple patterns like pattern 42 are formed on different areas of wafer 40 to enable more thorough and/or varied testing.

Figure 3A:
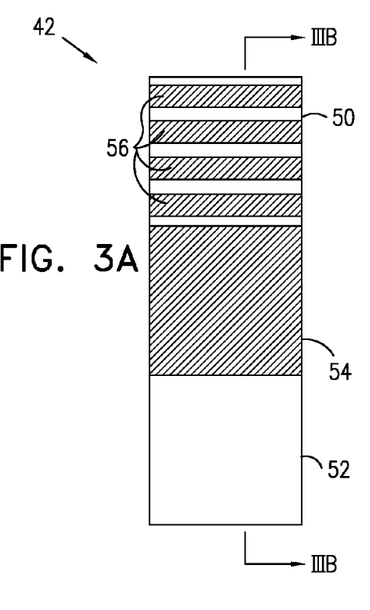
FIGS. 3A and 3B are top and sectional views, respectively, showing details of the test pattern of FIG. 2, in accordance with an embodiment of the present invention.
Figure 3B:
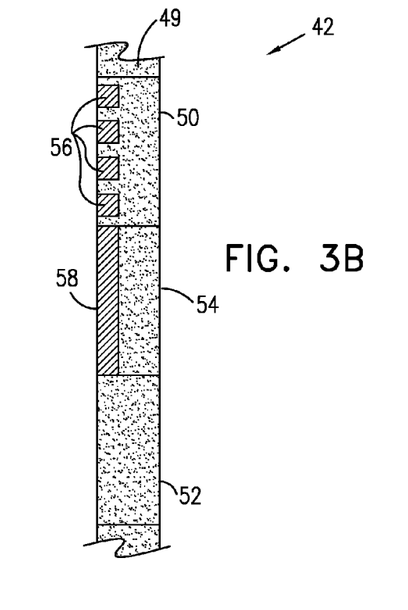

FIGS. 3A and 3B schematically show details of pattern 42 in top and sectional views, respectively, in accordance with an embodiment of the present invention. Pattern 42 is typically formed in an appropriate stage of processing of wafer 40, along with functional device features on dies 44, using photolithographic techniques, as are known in the art. In the present embodiment, the pattern is formed in a dielectric layer 49. Alternatively, the pattern may be produced in substantially any layer that is formed and etched, or otherwise patterned, on the surface of the wafer. Typically, pattern 42 is formed on a portion of wafer 40 with a clear substrate, i.e., without layers underlying the pattern that could confuse the measurements described hereinbelow.

Pattern 42 comprises three regions, which may be mutually-adjoining, as shown in the figure, or in close proximity one to another:

A test region 50, comprising a plurality of recesses 56. After the recesses have been etched, they are filled with another material or materials, in the same process steps and at the same time as vias and other recesses among the device features on dies 44 are filled. Thus, recesses 56 in region 50 are typically filled with multiple layers, such as a barrier layer and metal layers, but for the sake of simplicity, these multiple layers are not explicitly shown in FIG. 3B. The dimensions (depth and width of recesses 56 and the thickness of layers coating the recesses) are likely to be similar to those of nearby device features within dies 44.

A zero reference region 52. This region contains substantially none of the fill material.

A full-scale reference region 54. This region has a full coating 58 of the material, such as copper, with which recesses 56 are filled.

It is desirable that each of the regions be large enough (for example, at least 50×50 µm) so that the X-ray beam can be aimed and focused onto each region without substantially impinging on other regions.

The shapes and configurations of the regions shown in FIGS. 3A and 3B have been chosen only by way of illustration. Other arrangements of the regions, as well as other shapes and arrangements of recesses 56, will be apparent to those skilled in the art. For example, the recesses may be circular or rectangular (in the form of pads or tiles), or they may comprise square or circular through-holes, in addition to or instead of the elongated trenches shown in FIG. 3A. As another example, although it is convenient that reference region 54 have no recesses, as shown in the figures, the reference region may alternatively include recesses, as long as the pattern of recesses in the reference region is substantially different from that in the test region. (In this context and in the claims, the absence of recesses in reference region 54, as shown in FIGS. 3A and 3B, is considered to be a "different pattern of recesses" from that in test region 50.) Furthermore, although the present embodiment refers to regions of wafer 40 that are dedicated to test purposes, functional regions of dies 44 having appropriate patterns of recesses may be used alternatively or additionally for the testing purposes that are described herein.

The regions of pattern 42 may be used for various test purposes, including specifically measuring critical dimensions of features deposited on wafer 40 and assessing the effects of chemical-mechanical polishing (CMP) that is applied to such features, as described further hereinbelow. The width of recesses 56 (reflecting the critical dimension of functional structures in dies 46) can in principle be inferred from the XRF signals received from region 50 in system 20. The basis for this measurement is that the intensity of the X-ray fluorescence in the characteristic emission lines of the fill material (such as copper) is proportional to the amount of fill material in the recesses. Thus, the intensity of the fluorescence is proportional to the width of the recesses and can be used as an accurate measure of the width as long as the depth of the fill material in the recesses is known. When CMP or other techniques are used to remove some of the fill material after deposition, however, the thickness of the fill material is liable to change, thus undermining the accuracy of the critical dimension measurement.

In order to resolve this uncertainty, XRF measurements are also made on region 54. In this region, the X-ray fluorescence intensity is proportional only to the thickness of coating 58, since there is no width variation to be accounted for. The change in thickness due to CMP may be determined by measuring the X-ray fluorescence before and after polishing. Additionally or alternatively, the ratio of the intensity of fluorescence between regions 50 and 54 gives an indication of the width of recesses 56.

In order to enhance the accuracy of measurement, XRF intensities from regions 50 and 54 may be pre-calibrated using samples of known quality (for example, samples with over-etched, under-etched and properly-etched features, and samples that have been over-polished, under-polished and properly polished). The ratio of fluorescence intensities between regions 50 and 54 may be measured for all the different types of samples in order to define metrics that can be applied to determine critical dimensions and polishing effects from XRF measurements made on actual wafers in process. This sort of pre-calibration is particularly useful because CMP can affect layer thickness differently in patterned regions, such as region 50, by comparison with uniformly-coated regions, such as region 54.

Subsequent electrical testing of devices on dies 46 may also be used to correlate the XRF calibration standards and metrics described above with electrical performance of the devices.

Figure 4:
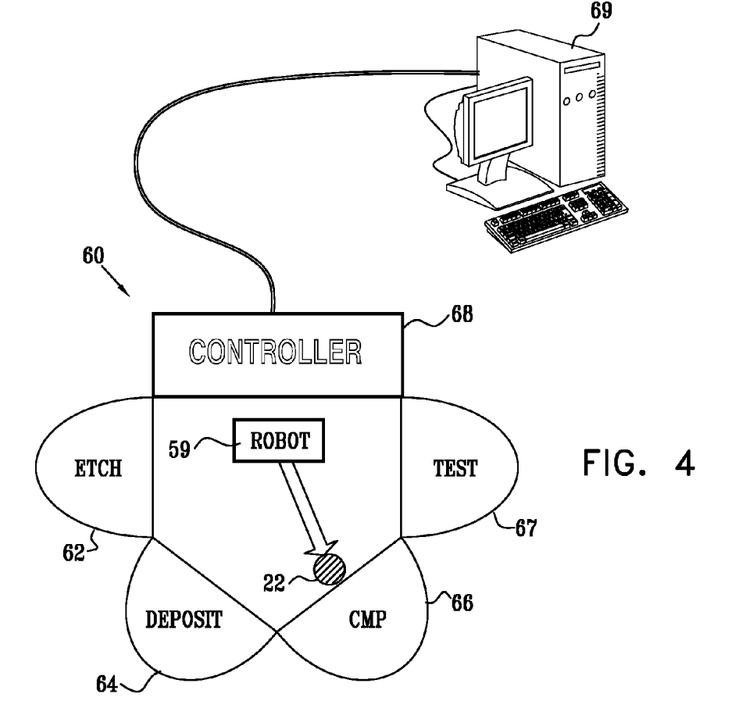
FIG. 4 is a schematic top view of a cluster tool for semiconductor device fabrication, including an inspection station in accordance with an embodiment of the present invention.

FIG. 4 is a schematic top view of a cluster tool 60 for use in semiconductor device fabrication, in accordance with an embodiment of the present invention. The cluster tool comprises multiple stations, including an etching station 62, for etching micro-structures in the surface of wafer 22; a deposition station 64, for depositing thin films on the wafer; a polishing station 66, which performs chemical-mechanical polishing (CMP) of the wafer surface; and a test station 67. Test station 67 operates in a manner similar to system 20 (FIG. 1), and thus applies the methods described hereinabove for evaluating critical dimensions and thickness of layers deposited on wafer 22. A robot 59 transfers the wafer among stations 62, 64, 66, 67, under the control of a system controller 68. Operation of tool 60 may be controlled and monitored by an operator using a workstation 69, coupled to controller 60.

Test station 67 may be used to perform X-ray inspection of wafers before and after selected steps in production processes carried out by etching station 62, deposition station 64, and CMP station 66 in tool 60. For example, the test station may apply XRF measurement to determine metal layer thickness and critical dimensions of wafer features after metal deposition by deposition station 64 and/or after polishing by CMP station 66. This arrangement allows early detection of process deviations and convenient adjustment and evaluation of process parameters on production wafers, using controller 68 and possibly workstation 69. The user of cluster tool 60 can choose the sequence of production and testing steps in order to optimize throughput and device quality. Alternatively, test station 67 may be operated as a standalone element in the semiconductor fab, separate from the processing chambers shown in FIG. 4. Further alternatively, XRF measurement may be performed in situ in one or more of the processing chambers.

Figure 5:
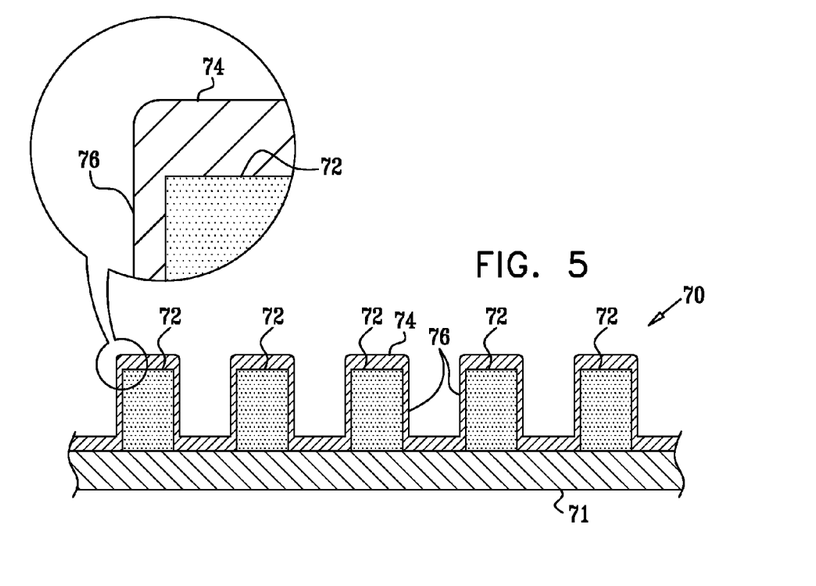
FIG. 5 is a schematic, sectional view of a periodic pattern on a sample surface, which is overlaid by a thin film layer, and which is tested in accordance with an embodiment of the present invention.

FIG. 5 is a schematic, sectional illustration of a pattern 70 formed on a substrate layer 71, whose characteristics are measured by means of XRF in accordance with another embodiment of the present invention. In this embodiment, pattern 70 comprises ridges 72, which are overlaid by a thin film layer 74. For example, layer 74 may comprise a diffusion barrier (such as Ta, TaN, TiN, or high-k dielectric), which is deposited over ridges 72 of oxide or semiconductor material before filling the gaps between the ridges with metal. The process by which layer 74 is deposited over pattern 70 must be carefully controlled so that the thickness of the layer is within the predefined process bounds, typically 10-20 Å. As another example, layer 74 may comprise a conformal high-k dielectric film used in producing on-chip capacitors.

As in the preceding embodiments, the intensity of X-ray fluorescence that is received from a region containing pattern 70 in an emission line of the material making up layer 74 is proportional to the amount of the material that is deposited on the surface of the sample. Assuming the width, depth and spacing of ridges 72 is known, geometrical considerations may be used to relate the total material volume determined from the intensity measurement to the thickness of layer 74. In one embodiment, the layer thickness is assumed to be constant over the entire surface of the sample, thus giving a simple linear relation between the XRF intensity and the layer thickness, depending on the total surface area of layer 74.

In practice, however, because of the geometry of the wafer and the deposition equipment, the thickness of the layer that is deposited on sidewalls 76 of ridges 72 is typically less than the thickness on the horizontal surfaces at the top and bottom of the ridges. It is therefore particularly useful to measure the sidewall layer thickness specifically. One way of estimating the sidewall layer thickness is using a model of deposition, which may be theoretical or empirically-derived, to estimate the ratio of the thickness of deposition on horizontal surfaces to that on the sidewalls. This ratio may then be used in a modified geometrical model for deriving the sidewall layer thickness from the XRF intensity.

As another alternative, the thickness of layer 74 on the horizontal surfaces of the sample may be measured separately, and then used to derive the sidewall layer thickness.

One way to determine the horizontal layer thickness is by measuring and comparing XRF intensity from different regions of the wafer surface having different patterns of recesses. For example, the XRF intensity emitted from a flat, uniformly-coated horizontal reference region, such as region 54 (FIG. 2A), may be measured in order to give the horizontal layer thickness, which may then be used in deriving the sidewall layer thickness from the measurement made in region 50.

As another alternative, X-ray reflectometry (XRR) may be used to directly measure the layer thickness on the horizontal surfaces, using XRR techniques that are known in the art, as described, for example, in the above-mentioned U.S. Pat. No. 6,381,303 or in U.S. Pat. No. 6,512,814, whose disclosure is incorporated herein by reference. This measured horizontal layer thickness may then be used together with the pattern geometry to determine the volume of layer 74 on the horizontal surfaces, which may then be subtracted from the total volume of layer 74 that is determined from the XRF measurement. The difference between these two measurements is approximately equal to the volume of the remaining portion of layer 74, which is deposited on sidewalls 76. The surface area of the sidewalls may be estimated based on the known geometry of ridges 72, whereupon the thickness of the layer on the sidewalls is given by the ratio of the volume to the surface area.

Figure 6:
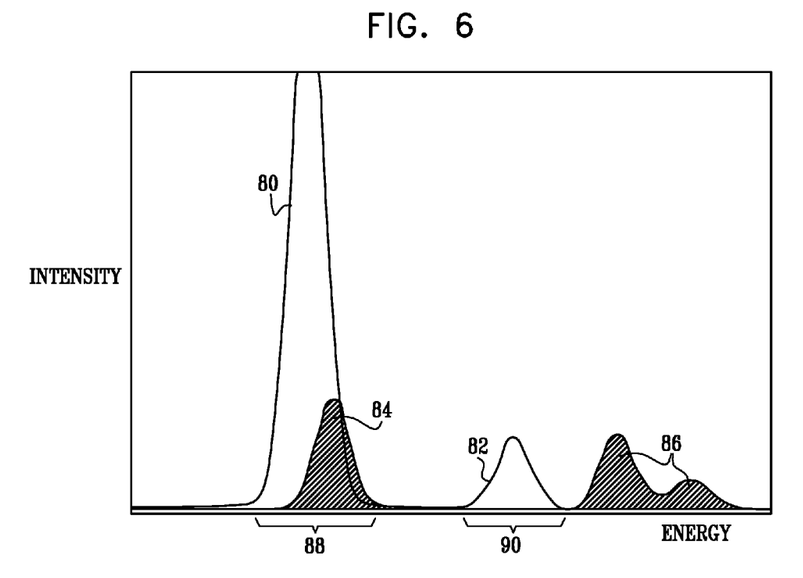
FIG. 6 is a schematic representation of an XRF spectrum captured by a system for X-ray microfluorescence measurement, in accordance with an embodiment of the present invention.

FIG. 6 is a schematic representation of an XRF spectrum captured by system 20, in accordance with an embodiment of the present invention. In this example, copper is deposited on an area of wafer 22 with a thin tantalum barrier layer. The copper layer emits X-ray fluorescence in the well-known Cu Kα1 line 80 and Cu Kβ1 line 82. The tantalum barrier layer emits X-ray fluorescence in Ta Lα1 line 84 and in Ta Lβ lines 86. The intensity of the Ta Lα1 line would generally give a good indication of the thickness of the tantalum layer that is deposited on the wafer, but in this case, Ta Lα1 is masked by the much stronger Cu Kα1 line.

In order to overcome this problem and assess the tantalum thickness, processor 34 computes the total XRF intensity in each of spectral regions 88 and 90. The intensity in region 90 is due to the copper layer alone. The intensity in region 88 is due to both copper and tantalum fluorescence. To estimate the tantalum thickness, a reference ratio of the intensities in regions 88 and 90 is determined in the absence of tantalum. (The reference ratio may be determined from first principles or may be measured using a reference wafer without a tantalum barrier layer.) The actual ratio of the measured intensities in regions 88 and 90 in the presence of the tantalum barrier layer is then compared to the reference ratio. The difference between the actual and reference ratios is attributable to the tantalum barrier layer, and the thickness of the tantalum may thus be estimated, even though the Ta Lα1 line itself cannot be resolved.

Figure 7:
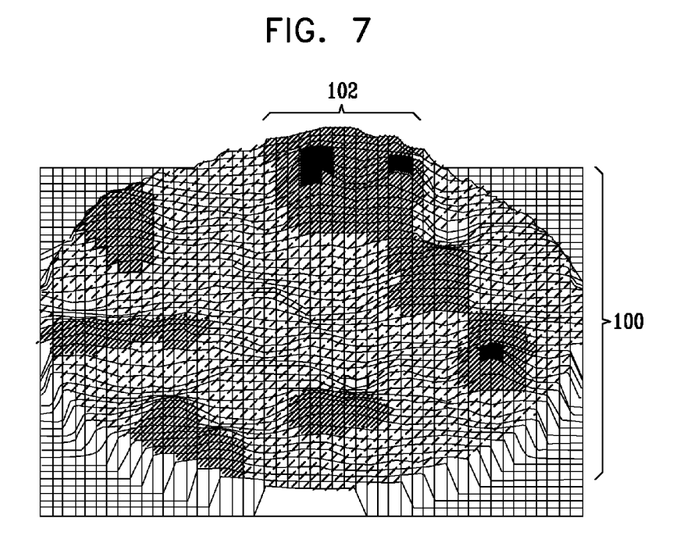
FIG. 7 is a plot that schematically shows the thickness of a barrier layer measured using X-ray microfluorescence measurement, in accordance with an embodiment of the present invention.

FIG. 7 is a plot that schematically shows the intensity ratio between regions 88 and 90, measured using the technique described above, in accordance with an embodiment of the present invention. This intensity ratio provides an assessment of the thickness of the tantalum barrier layer, as explained in the previous paragraph. The plot uses pseudo-color and elevation to show the distribution of intensity ratio, and thus of the thickness of tantalum deposition over an area 100 of wafer 22. In this manner, processor 34 is able to detect reduced tantalum coverage in certain regions of the wafer, such as a region 102. Although the technique of FIGS. 6 and 7 is described hereinabove with specific reference to tantalum and copper, the principles of this technique may similarly be applied in measuring the thickness of other elements in other multi-layer configurations in which layers of different elements having overlapping spectral lines are deposited on a substrate.

As an alternative or addition to the methods described above, other XRF-based methods, and particularly grazing emission XRF (GE-XRF) analysis, may be used in measuring layer dimensions, as described in the above-mentioned U.S. patent application Ser. No. 11/487,433. GE-XRF is described, for example, in an article by Wiener et al., entitled "Characterization of Titanium Nitride Layers by Grazing-Emission X-ray Fluorescence Spectrometry," in *Applied Surface Science* 125 (1998), p. 129, which is incorporated herein by reference. GE-XRF from a pattern of ridges overlaid by a thin film layer will give an angular spectrum with multiple side lobes, which can be analyzed to find the sidewall layer thickness.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for inspection of a sample, comprising:
    directing an excitation beam to impinge on an area of a planar sample that comprises a feature having sidewalls perpendicular to a plane of the sample, the sidewalls having a thin film thereon, wherein the area of the planar sample comprises a first region having one or more recesses formed in a first pattern in a surface layer thereof;
    directing the excitation beam to impinge on a second region of the planar sample having a second pattern of recesses, which is different from the first pattern;
    measuring an intensity of X-ray fluorescence (XRF) emitted from the sample responsively to the excitation beam; and
    assessing a thickness of the thin film on the sidewalls based on the intensity by comparing first and second intensities of the XRF emitted from the first and second regions, respectively.

2. The method according to claim 1, wherein the thin film is applied to at least one horizontal surface of the sample, in addition to the sidewalls, and wherein assessing the thickness comprises determining a depth of the thin film on the at least one horizontal surface, and calculating the thickness of the thin film on the sidewalls based on both the depth and the intensity.

3. The method according to claim 2, wherein determining the depth comprises measuring X-ray reflectance from the at least one horizontal surface.

4. The method according to claim 2, wherein determining the depth comprises depositing the thin film on a reference area of the planar sample that does not contain the sidewalls, and measuring the depth of the thin film on the reference area.

5. A method for inspection of a sample, comprising:
    directing an excitation beam to impinge on an area of a planar sample that comprises a feature having sidewalls perpendicular to a plane of the sample, the sidewalls having a thin film thereon;
    measuring an intensity of X-ray fluorescence (XRF) emitted from the sample responsively to the excitation beam; and
    assessing a thickness of the thin film on the sidewalls based on the intensity, wherein the sidewalls comprise a first element, which emits the XRF in a first XRF spectral line, and wherein a second element is also deposited on the area of the planar sample, the second element having second and third XRF spectral lines, wherein the third XRF spectral line overlaps the first XRF spectral line, and wherein assessing the thickness comprises measuring a ratio of a first intensity of the XRF measured in a first spectral region comprising the first and third XRF spectral lines to a second intensity of the XRF measured in a second region comprising the second XRF spectral line, and calculating the thickness based on the measured ratio.

6. The method according to claim 5, wherein calculating the thickness comprises comparing the measured ratio to a reference ratio determined for the second element in absence of the first element.

7. The method according to claim 5, wherein the first element is tantalum, and the second element is copper.

8. The method according to claim 1, wherein measuring the intensity comprises detecting an angular spectrum of grazing emission XRF.

9. A method for processing a sample, comprising:
depositing a material over first and second regions of the sample, the first region having one or more recesses formed in a first pattern in a surface layer thereof, while the second region is characterized by a second pattern of recesses, which is different from the first pattern;
polishing the sample after depositing the material so as to remove a portion of the material from the sample;
after polishing the sample, directing an excitation beam onto the first and second regions;
measuring first and second intensities of X-ray fluorescence emitted responsively to the excitation beam from the first and second regions, respectively, in a spectral range in which the material is known to fluoresce; and
assessing both a thickness of the material deposited in the recesses in the first pattern and a width of the recesses in the first pattern based on the first and second intensities.

10. The method according to claim 9, and comprising, prior to polishing the sample, directing the excitation beam onto at least the second region and measuring a third intensity of the X-ray fluorescence emitted responsively to the excitation beam, and determining a quantity of the material removed by the polishing based on a difference between the second and third intensities.

11. The method according to claim 9, wherein the second pattern is planar and contains none of the recesses.

12. The method according to claim 9, and comprising measuring a third intensity of the X-ray fluorescence emitted responsively to the excitation beam from a third region on which the material is not deposited, and wherein assessing both the thickness and the width comprises using the measured third intensity as a zero reference in determining the thickness and the width.

13. The method according to claim 9, wherein the recesses in the first region are formed so as to define at least one feature selected from a group of features consisting of lines, pads, tiles and through-holes.

14. Apparatus for inspection of a sample, comprising:
an excitation source, which is configured to direct an excitation beam to impinge on an area of a planar sample that comprises a feature having sidewalls perpendicular to a plane of the sample, the sidewalls having a thin film thereon;
one or more detectors, which are arranged to measure an intensity of X-ray fluorescence (XRF) emitted from the sample responsively to the excitation beam; and
a signal processor, which is operative to assess a thickness of the thin film on the sidewalls based on the intensity,
wherein the sidewalls comprise a first element, which emits the XRF in a first XRF spectral line, and wherein a second element is also deposited on the area of the planar sample, the second element having second and third XRF spectral lines, wherein the third XRF spectral line overlaps the first XRF spectral line, and
wherein the signal processor is adapted to assess a ratio of a first intensity of the XRF measured in a first spectral region comprising the first and third XRF spectral lines to a second intensity of the XRF measured in a second region comprising the second XRF spectral line, and to calculate the thickness based on the measured ratio.

15. The apparatus according to claim 14, wherein the thin film is applied to at least one horizontal surface of the sample, in addition to the sidewalls, and wherein the signal processor is arranged to determine a depth of the thin film on the at least one horizontal surface, and to calculate the thickness of the thin film on the sidewalls based on both the depth and the intensity.

16. Apparatus for inspection of a sample, comprising:
an excitation source, which is configured to direct an excitation beam to impinge on an area of a planar sample that comprises a feature having sidewalls perpendicular to a plane of the sample, the sidewalls having a thin film thereon;
one or more detectors, which are arranged to measure an intensity of X-ray fluorescence (XRF) emitted from the sample responsively to the excitation beam; and
a signal processor, which is operative to assess a thickness of the thin film on the sidewalls based on the intensity,
wherein the area of the planar sample comprises a first region having one or more recesses formed in a first pattern in a surface layer thereof, and
wherein the excitation source is arranged to direct the excitation beam to impinge on a second region of the planar sample having a second pattern of recesses, which is different from the first pattern, and
wherein the signal processor is adapted to assess the thickness by comparing first and second intensities of the XRF emitted from the first and second regions, respectively.

17. Apparatus for processing a sample, comprising:
a deposition station, which is arranged to deposit a material over first and second regions of the sample, the first region having one or more recesses formed in a first pattern in a surface layer thereof, while the second region is characterized by a second pattern of recesses, which is different from the first pattern;
a polishing station, which is arranged to polish the sample after depositing the material so as to remove a portion of the material from the sample; and
a test station, which is arranged to direct an excitation beam onto the first and second regions after polishing of the sample, to measure first and second intensities of X-ray fluorescence emitted responsively to the excitation beam from the first and second regions, respectively, in a spectral range in which the material is known to fluoresce, and to assess both a thickness of the material deposited in the recesses in the first pattern and a width of the recesses in the first pattern based on the first and second intensities.

18. Apparatus for inspection of a sample, comprising:
an excitation source, which is configured to direct an excitation beam onto first and second regions of the sample after deposition of a material over the first and second regions of the sample, the first region having one or more recesses formed in a first pattern in a surface layer thereof, while the second region is characterized by a second pattern of recesses, which is different from the first pattern, and after polishing of the sample so as to remove a portion of the material from the sample following the deposition of the material;

one or more detectors, which are arranged to measure first and second intensities of X-ray fluorescence emitted responsively to the excitation beam from the first and second regions, respectively, in a spectral range in which the material is known to fluoresce; and a signal processor, which is operative to assess both a thickness of the material deposited in the recesses in the first pattern and a width of the recesses in the first pattern based on the first and second intensities.

* * * * *